(12) United States Patent
Bottazzo et al.

(10) Patent No.: US 8,063,011 B2
(45) Date of Patent: Nov. 22, 2011

(54) PREDICTION AND PROPHYLACTIC TREATMENT OF TYPE 1 DIABETES

(75) Inventors: Gian Franco Bottazzo, Rome (IT); Mattia Locatelli, Berbenno (IT)

(73) Assignees: Gian Franco Bottazzo, Rome (IT); Mattia Locatelli, Berbenno (IT); Lamya Al-Saqqaf, Rome (IT)

( * ) Notice: Subject to any disclaimer, the term of this patent is extended or adjusted under 35 U.S.C. 154(b) by 0 days.

(21) Appl. No.: 12/375,411

(22) PCT Filed: Jul. 30, 2007

(86) PCT No.: PCT/IB2007/003024
§ 371 (c)(1),
(2), (4) Date: Jan. 28, 2009

(87) PCT Pub. No.: WO2008/035204
PCT Pub. Date: Mar. 27, 2008

(65) Prior Publication Data
US 2010/0137393 A1 Jun. 3, 2010

(30) Foreign Application Priority Data
Jul. 28, 2006 (GB) .................................. 0615063.5

(51) Int. Cl.
*A61K 38/00* (2006.01)
(52) U.S. Cl. .......................................... 514/1.1; 514/866
(58) Field of Classification Search .................. 424/439; 514/2, 866, 1.1
See application file for complete search history.

(56) References Cited

U.S. PATENT DOCUMENTS

| 2002/0064549 | A1 | 5/2002 | Shehadeh |
| 2006/0088574 | A1* | 4/2006 | Manning et al. ............... 424/439 |
| 2008/0026378 | A1 | 1/2008 | Bottazzo |

FOREIGN PATENT DOCUMENTS

| WO | 02/13814 A1 | 2/2002 |

OTHER PUBLICATIONS

Locatelli et al. (Diabetologia Aug. 2005 vol. 48 p. 114).*
WO 2008/035204 A3, International Search Report in International Application No. PCT/IB2007/003024 from which the present application is a U.S. National Stage application.
Locatelli, M. et al. "Children Who Develop Type 1 Diabetes Early in Life Have Low Levels of Carnitine and Amino Acids at Birth: Does This Finding Shed Light on the Etiopathogenesis of the Disease?," Diabetologia, vol. 48, No. suppl. 1, Aug. 2005, pp. 114-114.
Buzzetti, R., et al. "Genetic Prediction of Type 1 Diabetes in a Population with Low Frequency of HLA Risk Genotypes and Low Incidence of the Disease (the DIABFIN study)," Diabetes/Metabolism Research and Reviews, vol. 20, 2004, pp. 137-143.
Emery, L.M., et al. "Newborn HLA-DR, DQ genotype screening: age- and ethnicity-specific type 1 diabetes risk estimates," Pediatr Diabetes, vol. 6, No. 3, Sep. 2005, pp. 136-144.
Marks, J.B. "In Pursuit of Type 1 Diabetes Prevention" Clinical Diabetes, vol. 20, No. 4, 2002, pp. 168-169.
Williams, R., et al. "The Evidence Base for Diabetes Care—Part II: Prevention of Diabetes," 2002.
DeLuca, G. et al. "Preliminary Report: Amino Acid Profile in Platelets of Diabetic Patients," Metabolism, vol. 50, No. 7, Jul. 2001, pp. 739-741.
Mamoulakis, D. et al. "Carnitine Deficiency in Children and Adolescents with Type 1 Diabetes," J. of Diabetes and Its Complications, vol. 18, No. 5, Sep. 2004, pp. 271-274.
Devendra et al, "Type 1 diabetes: recent developments," BMJ Mar. 27, 2004, vol. 328, p. 750.
Wittaker et al., "Whole body protein kinetics in women: effect of pregnancy and IDDM during anabolic stimulation," American J Physiol Endocrinal Metab, 200 vol. 279 p. E978.
Wijekoon et al., "Amino acid metabolism in the Zucker diabetic fatty rat: effects of insulin resistance and of type 2 diabetes," Can J. Phyysiol Pharmacol. 2004 vol. 82, p. 506.
Action in related U.S. Appl. No. 11/496,001, dated Mar. 4, 2010.
IPRP in parent PCT application PCT/IB2007/003024.
Written Opinion and ISR in parent PCT application PCT/IB2007/003024.
Co-pending U.S. Appl. No. 11/496,001 to which the present application claims priority, and the file wrapper thereof. Although the application and file wrapper are available to the Office, Applicant submits herewith a courtesy Restriction Requirement and Notice mailed during the prosecution of that matter.
Jay S. Skyler, Prevention of Type 1 Diabetes, The Evidence Base for Diabetes Care, 2002, pp. 44-68, John Wiley & Sons, Ltd.
Akerblom, HK Vaarala O, Hyoty H., Ilonen J., Knip M., "Environmental factors in the etiology of type 1 diabetes.", (2002), Am J. Med. Genet., May 30; 115(1): 18-29.
Virtanen SM, Knip M., "Nutritional risk predictors of beta cell autoimmunity and type 1 diabetes at a young age." (2003) Am. J. Clin. Nutr., Dec; 78(6): 1053-67.
Ziegler AG, Schmid S., Huber D., Hummel M., Bonifacio E., "Early infant feeding and risk of developing type 1 diabetes-associated autoantibodies." (2003) J. Am. Med. Assoc., Oct. 1; 290(13):1721-8.
Redondo MJ, Fain PR, Eisenbarth GS, "Genetics of type 1A diabetes" (2001) Recent Prog. Horm. Res. 56: 69-89.
Ilonen J., Sjoroos M, Knip M, Veijola R, Simell O, Akerblom HK, Paschou P, Bozas E, Havarani B, Malamitsi-Puchner A, Thymelli J, Vazeou A, Bartsocas CS (2002) "Estimation of genetic risk for type 1 diabetes," Am. J. Med. Genet. 115(1):30-6.

(Continued)

Primary Examiner — Kevin E Weddington
(74) Attorney, Agent, or Firm — Kristina Castellano; Castellano PLLC

(57) ABSTRACT

An in vitro method for predicting the onset of type 1 diabetes (T1 D) in a subject, comprises the steps of: (a) measuring the concentration of at least one amino acid, amino acid derivative or amino acid metabolite in a biological sample taken from the subject; (b) determining the subject's HLA genotype; (c) assigning the subject's genetic risk of developing T1 D on the basis of the subject's HLA genotype; (d) combining the information obtained in step (a) with the information in step (c); and (e) predicting the likelihood of onset of T1 D based upon the combination of step (d). The diagnostic method can be used to select target subjects for T1 D prophylactic treatment, and as part of a T1 D preventative treatment regime for neonates having a likelihood of developing childhood T1 D.

3 Claims, 4 Drawing Sheets

OTHER PUBLICATIONS

Mimbacas A., Perez-Bravo F, Hidalgo PC, Javiel G, Pisciottano C, Grignola R, Jorge AM, Gallino JP, Gasagoite J, Cardoso H. (2003) "Association between diabetes type 1 and DQB1 alleles in a case-control study conducted in Montevideo, Uruguay," Genet. Mol. Res. 2(1):29-35.

Lambert AP, Gillespie KM, Thompson G, Cordell HJ, Todd JA, Gale EA, Bingley PJ, "Absolute risk of childhood-onset type 1 diabetes defined by human leukocyte antigen class II genotype: a population-based study in the United Kingdom." (2004) J. Clin. Endocrinol. Metab. 89(8):4037-43.

Buzzetti R, Galgani A, Petrone A, Del Buono MI, Erlich HA, Bugawan TL, Lorini R, Meschi F, Multari G, Pozzilli P, Locatelli M, Bottazzo G, Di Mario U, "Genetic prediction of type 1 diabetes in a population with low frequency of HLA risk genotypes and low incidence of the disease (the DIABFIN study)" (2004), Diabetes Metab. Res. Rev., Mar.-Apr.; 20(2): 137-43.

Galgani A, Petrone A, Spoletini M, Hodge A, Del Buono ML, Locatelli M, Buzzetti R and the Diabfin Study Group. "HLA class II typing in newborns reveals a low frequency of the DRBI*04 allele and a high frequency of DRB1*11 allele in three regions of continental Italy." (2004) Hum. Immuniol. 65(4): 366-72.

* cited by examiner

PREDICTION AND PROPHYLACTIC TREATMENT OF TYPE 1 DIABETES

CROSS REFERENCE TO RELATED APPLICATION

This application is a U.S. National Phase Application based on PCT/IB2007/003024 filed on Jul. 30, 2007, which claims the benefit of U.S. application Ser. No. 11/496,001 filed on Jul. 28, 2006, and Great Britain application No. 0615063.5, the contents of each of which are hereby incorporated by reference in their entirety.

FIELD

This invention relates to methods for the prediction of type 1 diabetes, and in particular, to a method for predicting the probable onset of type I diabetes in children by measuring circulating levels of metabolites in blood, and also to methods for the prophylactic treatment of type 1 diabetes.

BACKGROUND

Diabetes mellitus ("diabetes") is a medical disorder characterized by persistent variable hyperglycemia (i.e. high blood sugar levels). It can result from either inadequate secretion of the hormone insulin, an inadequate response by the body to insulin, or a combination of these factors. The most common forms of diabetes are type 1, type 2 and gestational diabetes.

Type 1 diabetes (T1D, also known as "childhood", "juvenile" or "insulin-dependent" diabetes) is most commonly diagnosed in children and adolescents. It is an autoimmune disorder, in which the patient's own immune system attacks the beta cells in the Islets of Langerhans of the pancreas—where insulin is produced, and/or the insulin molecule itself. Consequently, patients with clinical T1D require regular insulin replacement therapy, immunosuppression treatment or even more experimental therapies such as islet transplantation and stem cell therapy. However, none of these treatments are ideal. While insulin replacement therapy and immunosuppression require long term treatment and cannot eradicate all diabetes induced complications, islet transplantation and stem cell therapy are not widely available and are very expensive.

Throughout the world the percentage incidence of T1D is increasing, and this is especially true of the early onset form of T1D, which affects children under the age of 4 yrs. Currently in North America T1D affects approximately 1 in 300 people and accounts for approximately 10% of all diabetic cases.

T1D is a multigenetic disorder, with up to 20 genes known to contribute. Of these, the major genetic susceptibility determinants are the human leukocyte antigen (HLA) class II alleles, HLA-DR and HLA-DQ, which are associated with up to 50% of all T1D cases. However, genetic factors alone cannot account for a person's susceptibility to the disease. For instance, less than 10% of new T1D patients have an affected family member, while the concordance between genetically identical twins is only approximately 50%. In addition, the incidence of T1D is rising far too rapidly to be attributed merely to the inheritance of diabetogenic genes. Thus, it is widely acknowledged that non-genetic, environmental factors (e.g. nutrition, infectious agents) must also play an important role in either the triggering or progression of the disease process, or both.

Indeed, several prospective studies have suggested that factors operating early in life may play an important role in the etiopathogenesis of T1D (Akerblom H. K. Vaarala O, Hyoty H, Ilonen J, Knip M., Environmental factors in the etiology of type 1 diabetes, 2002, *Am. J. Med. Genet.* May, 115(1), 18-29). Amongst the environmental factors that may be involved, dietary factors operating early in life, i.e. short breast feeding, early exposure to cow's milk, early introduction of gluten, have been suggested to increase the risk of developing the disease (Virtanen S. M. & Knip M. Nutritional risk predictors of beta cell autoimmunity and type 1 diabetes at a young age, 2003, *Am. J. Clin. Nutr.*, December, 78(6), 1053-1067; and Ziegler A. G. Schmid S, Huber D, Hummel M, Bonifacio E., Early infant feeding and risk of developing type 1 diabetes-associated autoantibodies, 2003, *J. Am. Med. Assoc, October,* 290(13), 1721-1728).

The non-genetic factors that contribute to T1D susceptibility are even less well defined than the genetic factors. In particular, there is little verifiable evidence of the specific contribution of non-genetic factors to T1D or how such factors interact with and influence the known genetic predeterminants.

The clinical onset (i.e. the insulin-dependent stage) of T1D is preceded by a sub-clinical phase, that can last up to several years, during which the insulin-producing islet cells and/or the patient's insulin are progressively destroyed. The sub-clinical phase is typically characterized by the presence of autoantibodies, which target one or more of the subject's islet cells (islet cell antibodies, ICAs), insulin (insulin autoantibodies, IAAs), glutamic acid decarboxylase (glutamic acid decarboxylase autoantibodies, GADAs) and tyrosine phosphatase (tyrosine phosphatase autoantibodies, IA-2As). Accordingly, there is potentially a window of opportunity during which subjects at risk of T1D may be identified for preventative therapy.

Increasingly, combinations of markers are being used to better define the risk of diabetes. However, while the detection of two or more types of autoantibody (ICA, IAA, GADA and IA-2A) has been linked to the future onset of diabetes, significant problems remain in the selection and identification of subjects having a high probability of developing T1D, and especially of children vulnerable to the early-onset form.

In this regard, until now, the selection of candidates for T1D predictive testing has largely focused on those subjects who have a family member already with the disease. However, with a less than 10% familial correlation, this approach is entirely inadequate to provide an effective means of identifying 90% of eventual T1D patients for intervention therapy. Hence, there is a need for a reliable, effective and simple method for predicting susceptibility or predisposition to T1D, that can be readily used for large-scale screening of the general population, rather than of specific genetic sub-groups.

Although children who develop early-onset T1D (i.e. in the period 0-4 yrs) may show signs of IAAs even from birth, it is not possible to distinguish neonatal autoantibodies from transplacental maternal IgGs in the first year of life. Accordingly, of those neonatal children tested and found positive for particular autoantigens, the vast majority may not ultimately develop T1D.

BRIEF DESCRIPTION OF THE DRAWINGS

The invention is further illustrated by the accompanying drawings in which.

DETAILED DESCRIPTION

Figure 1:
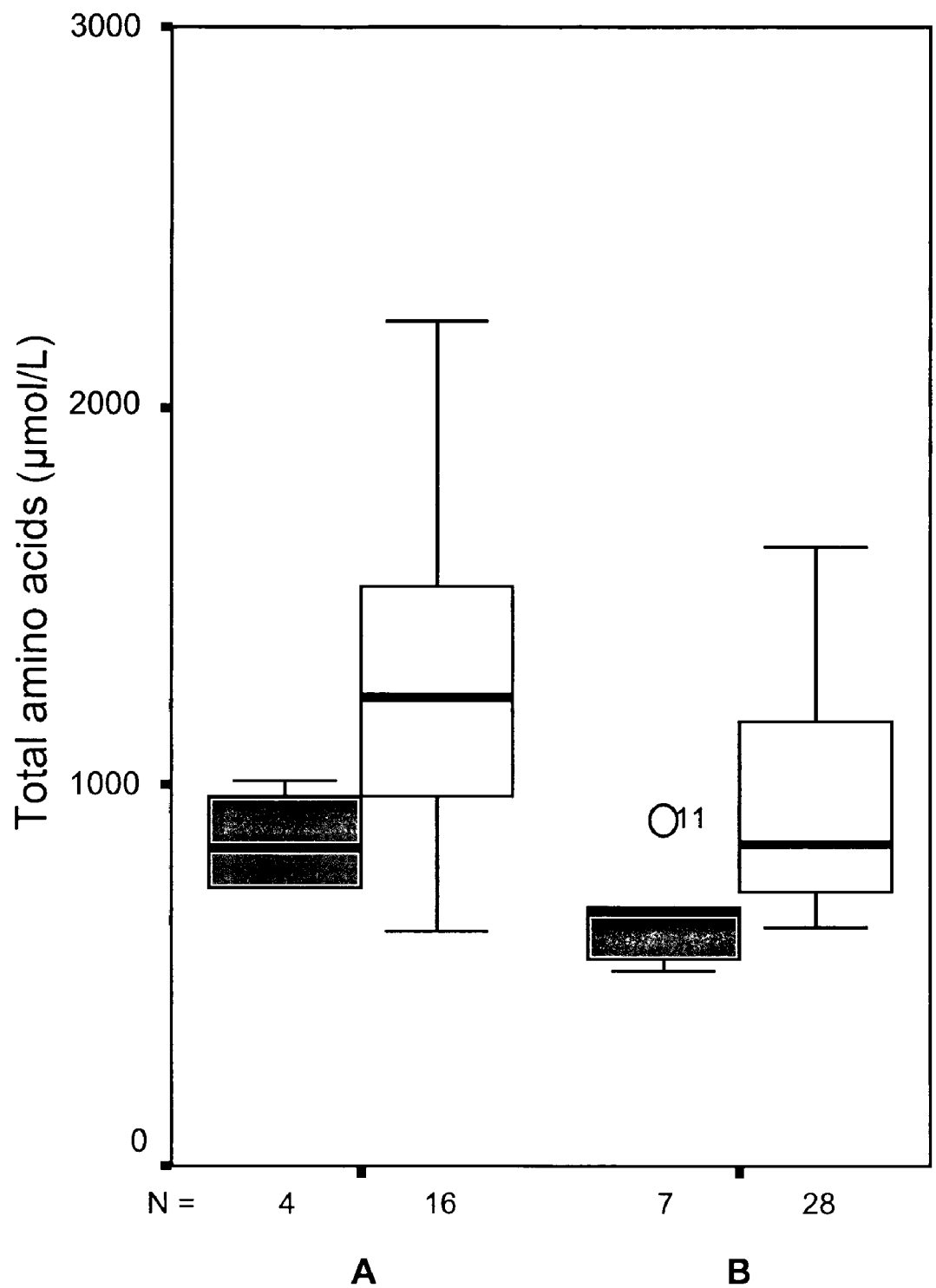
FIG. 1 is a graph showing the relationship between the total concentration of amino acids (vertical axis) in blood samples taken from T1D patients (grey-filled boxes and associated bars) and non-diabetic negative controls (open boxes and associated bars), in comparison to their HLA genotype risk category (horizontal axis): high HLA genetic risk category patients (A); and medium/moderate and low HLA genetic risk categories, grouped together (B). The boxes indicate the $75^{th}$ percentile (top of box) and the $25^{th}$ percentile (bottom of box). The number of subjects in each group is shown along the horizontal axis (N).

In view of the rising incidence of T1D in children, the lack of a suitable method for predicting the likely onset of T1D in children, and in view of the potential for an early intervention therapy if it is predicted sufficiently early in children, it would be particularly desirable to have an effective method of predicting T1D in children, especially in the first few days of life.

Moreover, given the current lack of a definitive cure for T1D, the need for frequent, tightly controlled medication, and the potentially fatal consequences of a lapse in the treatment regime, the most important driver for detecting individuals who are at risk of developing T1D is the potential for a preventative therapy. Thus, it would be desirable to provide a prophylactic treatment regime for preventing or at least delaying the onset of T1D.

This invention aims to overcome or alleviate the problems associated with the prior art.

In light of the above, in prospective studies into the development of early-onset T1D, the inventors have surprisingly found that neonatal children who go on to develop T1D before the age of 4 yrs, display reduced levels of circulating amino acids in the first few days of life (e.g. 0-3 days), compared with children who do not develop T1D. Significantly, this trend is apparent irrespective of whether the subject has a low, moderate or high genetic predisposition to T1D based on his or her HLA genotype.

Thus, in accordance with a first aspect of the invention, there is provided an in vitro method for predicting the onset of type 1 diabetes (T1D) in a subject, comprising the steps of:

(a) measuring the concentration of at least one amino acid, amino acid derivative or amino acid metabolite in a biological sample taken from the subject;

(b) determining the subject's HLA genotype;

(c) assigning the subject's genetic risk of developing T1D on the basis of the subject's HLA genotype;

(d) combining the information obtained in step (a) with the information in step (c); and (e) predicting the likelihood of onset of T1D based upon the combination of step (d).

The amount of one or more amino acid can be measured in a number of relatively simple, quick and cost-effective ways, making the method of the invention a simple, reliable, quick and economical way of predicting the likelihood of future onset of T1D in a subject.

Thus, compared with prior art processes for predicting the development of T1D, the method of the invention has the advantage that it can be performed universally (i.e. on any subject, not just those whom have already been identified as being within a genetically high-risk group).

Indeed, the inventors have surprisingly found that the method of the invention can be used to predict the likelihood of onset of T1D in any member of the population, for example, subjects whom, according to their genetic markers, may be classified as "high", "moderate"/"medium" or "low" risk. Preferably, the genetic risk is classified according to the subject's HLA genotype.

The risk of developing T1D associated with particular HLA genotypes has been reported by a number of research groups (Redondo M. J. Fain P R, Eisenbarth G S, "Genetics of type 1A diabetes," 2001, *Recent Prog. Horm. Res.* 56: 69-89; Ilonen J. Sjoroos M, Knip M, Veijola R, Simell O, Akerblom H K, Paschou P, Bozas E, Havarani B, Malamitsi-Puchner A, Thymelli J, Vazeou A, Bartsocas C S, "Estimation of genetic risk for type 1 diabetes," 2002, *Am. J. Med. Genet.* 115(1): 30-6; Mimbacas, A. Perez-Bravo F, Hidalgo P C, Javiel G, Pisciottano C, Grignola R, Jorge A M, Gallino J P, Gasagoite J, Cardoso H., "Association between diabetes type 1 and DQB1 alleles in a case-control study conducted in Montevideo, Uruguay," 2003, *Gen. Mole. Res.*, 2(1), 29-35; Lambert, A. P. Gillespie K M, Thomson G, Cordell H J, Todd J A, Gale E A, Bingley P J., "Absolute risk of childhood-onset type 1 diabetes defined by human leukocyte antigen class II genotype: a population-based study in the United Kingdom," 2004, *J. Clin. Endocrinol. Metab.*, 89(8), 4037-4043; and Buzzetti R. Galgani A, Petrone A, Del Buono M L, Erlich H A, Bugawan T L, Lorini R, Meschi F, Multari G1 Pozzilli P, Locatelli M, Bottazzo G, Di Mario U., "Genetic prediction of type 1 diabetes in a population with low frequency of HLA risk genotypes and low incidence of the disease (the DIABFIN study)," 2004, *Diabetes Metab. Res. Rev.*, 20(2), 137-143).

The skilled person in the art will appreciate that since the method of the invention is applicable to subjects having high, medium or low risk HLA genotypes, the method of assigning such high, medium or low genetic risk categories is not essential to the performance of the invention. Preferably, however, the subject is assigned a genetic risk according to categorization reported in Buzzetti R. et al. (2004, *Diabetes Metab. Res. Rev.*, March-April, 20(2), 137-143), the teaching of which is incorporated herein in its entirety.

Hence, a high risk HLA genotype typically comprises the genetic markers:

DRB1*03/*04(not 0403), DQB1 0302.

A moderate or medium risk HLA genotype typically comprises the genetic markers:

DRB1*04(not 0403)/*04(not 0403), DQB1 0302;
DRB1*04 not 0403)/X, DQB1 0302/DQB1 not 0602-3)
DRB1*03/*03; and
DRB1*03/X, DQB1 not 0602-3, not 0301, not 0503;
wherein X is not DRB1*03, *04, or 0403.

A low risk HLA genotype comprises any combination of genetic markers not specified above.

In step (a) of the first aspect of the invention, the concentration of one or more amino acid, and/or amino acid derivative and/or amino acid metabolite is measured in a sample taken from a subject.

The term "amino acid" within the scope of the present invention is used in its broadest sense and is meant to include naturally occurring L α-amino acids or residues. The commonly used one and three letter abbreviations for naturally occurring amino acids are used herein (Lehninger, A. L., 1975, Biochemistry, 2d ed., pp. 71-92, Worth Publishers, New York). The general term "amino acid" further includes D-amino acids, where such occur naturally in the human or animal body. The term amino acid also encompasses naturally occurring amino acids that are not usually incorporated into proteins such as norleucine.

There are 20 common, naturally occurring amino acids that form the building blocks of human proteins, namely: alanine (Ala, A), arginine (Arg, R), asparagines (Asn, N), aspartic acid (aspartate, Asp, D), cysteine (Cys, C), glutamic acid (glutamate, Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Eight amino acids are generally regarded as essential for humans: tryptophan, lysine, methionine, phenylalanine, threonine, valine, leucine, and isoleucine. This means that they cannot be synthesized de novo within the human body. Two others, histidine and arginine are often considered to be essential in children and possibly also in the elderly, because they cannot be synthesized at a sufficient rate to meet the body's needs.

Furthermore, in some case, the distinction between essential and non-essential amino acids is a little blurred, because some amino acids can in fact be produced from others. For example, the sulfur-containing amino acids, methionine and homocysteine, can be converted into each other but neither can be synthesized de novo in humans. Likewise, cysteine can be made from homocysteine, but cannot be synthesized on its own. Hence, for convenience, sulfur-containing amino acids may sometimes be considered as a single pool of nutritionally-equivalent amino acids. Similarly, arginine, ornithine, and citrulline, which are interconvertible via the urea cycle, are sometimes considered to be a single group of amino acids.

As used herein, the "essential" amino acids are the 8 first listed above, and in the case of a neonate, the essential amino acids also include histidine and arginine.

The remaining 10 or 12 of the above-listed 20 amino acids are considered herein as "non-essential" amino acids in humans, which means that they can be synthesized de novo in the human body.

Other examples of amino acids are listed by Roberts and Vellaccio, The Peptides: Analysis, Synthesis, Biology, Gross and Meiehofer, eds., Vol. 5 p. 341, Academic Press, Inc., N.Y. 1983, which is incorporated herein by reference.

As used herein, the terms amino acid "derivative" or "metabolite" refer to naturally occurring, amino acids or small peptides, which do not fall within the 20 amino acids (above) that occur commonly in natural proteins and peptides. Such derivatives include, for example, chemically modified amino acids, dipeptides (molecules that are based on two covalently bonded amino acids) and tripeptides (molecules that are based on three covalently bonded amino acids), which are typically synthesized by the breakdown of proteins or the assembly of free amino acids in the human body. Examples of amino acid derivatives include carnitine, acylcamitine, glutathione, ornithine, taurine, citrulline, hydroxyproline, gamma-amino-butyric acid, cystine and aminoacetic acid. Amino acids metabolites are naturally occurring compounds that are produced as intermediates or as by-products in the biosynthesis of amino acids or of amino acid derivatives, and include, for example oxoglutarate and creatine. For the purposes of this invention, the terms "derivative" and "metabolite" are not exclusive, in the sense that some amino acid derivatives may also be considered to be amino acid metabolites, e.g. taurine.

Preferably in the methods of the invention, the one or more amino acid, amino acid derivative or amino acid metabolite whose concentration is measured, is selected from the group consisting of: alanine, arginine, aspartate, citrulline, glycine, glutamate, glutamine, leucine, isoleucine, methionine, ornithine, phenylalanine, proline, tyrosine and valine.

More preferably, in step (a) of the methods of the invention, the concentration of two or more amino acids, amino acid derivatives or amino acid metabolites are measured. Still more preferably, in step (a) the concentration of essential amino acids or of non-essential amino acids is measured.

Most preferably, the total concentration of all 15 of the amino acids, amino acid derivatives and amino acid metabolites of the above preferable embodiment of the invention is measured.

The concentration of amino acids, amino acid derivatives and amino acid metabolites in a sample taken from a subject can be measured using any suitable means/equipment known to the person of skill in the art. First, sample size may be calculated using standard procedures. In one embodiment, the sample size or volume is controlled, predetermined, measured, or otherwise known. For example, the sample may be collected using, or transferred to (as appropriate), a collection device that is only capable of collecting or extracting a specific, predetermined amount or volume of a biological sample, such as a syringe or a capillary. Thus, the sample volume may be controlled at the time of collection from the donor or at a later time from a sample already obtained from the donor individual. Alternatively, it may be suitable to drop or transfer a sample to a medium (for example, a matrix), which is only able to adsorb or hold a specific amount or volume of the sample. Any convenient predetermined sample size may be used, for example a sample may be between 10 and 200 µl or between 25 and 100 µl, such as approximately 50 µl. In another embodiment, it may be assumed that a drop of the sample, for example, of blood has a particular relatively consistent average volume. By way of example, in some embodiments a drop of blood may be considered to have a volume of approximately 50 µl.

Conveniently the means of measuring concentration will be capable of measuring more than one such amino acid, amino acid derivative or amino acid metabolite in a single sample at the same time. Advantageously, the technique used will be relatively rapid, for example, capable of generating results (or at least allowing the interpretation of the results) within 24 hours of the start of the procedure. Preferably, the technique will be capable of analyzing samples in a high-throughput manner, to allow the processing of a plurality of samples in a day. Furthermore, it is beneficial for the equipment used to be widely available so that it is possible to readily analyze samples in appropriate regions of the world. For example, suitable means for measuring the concentrations of amino acids, amino acid derivatives and amino acid metabolites include mass spectrophotometry (e.g. tandem mass spectrometry) and HPLC. Preferably, tandem mass spectrometry is used, for the reasons given above.

In accordance with the invention, a likelihood of onset of T1D in a subject is predicted on the basis of the measured concentration of one or more amino acid, amino acid derivative or amino acid metabolite in a sample taken from the subject in view of the subject's HLA genotype risk category. Advantageously, the methods of the invention can be used to predict the onset of T1D whatever the HLA genotype risk category of the subject, and it is therefore suitable for entire population screening.

The likelihood of onset of T1D is thus a function of the subject's HLA genotype and the relative concentration of the amino acids, amino acid derivatives or amino acid metabolites. As such, the method provides a distinct advantage over predictions based on a subject's genotype only, which as suggested above can largely ignore non-genetic (e.g. environmental) factors that influence a person's probability of developing T1D.

Thus, where the subject has the high risk HLA genotype (as defined above), a likelihood of onset of T1D can be predicted when the subject's total concentration of alanine, arginine, aspartate, citrulline, glycine, glutamate, glutamine, leucine, isoleucine, methionine, ornithine, phenylalanine, proline, tyrosine and valine is less than approximately 1200 µmol/L, less than 1100 µmol/L, less than 1000 µmol/L, or less than 900 µmol/L.

Preferably, the amino acid concentration in a subject having a high risk HLA genotype is indicative of a likelihood of onset of T1D, where the above total amino acid concentration is in the range of 500-1200 µmol/L, 600-1100 µmol, 700-1000 µmol/L, or 800-900 µmol/L.

Most preferably, the total amino acid concentration for a subject with the high risk HLA genotype is approximately 850 µmol/L.

Where the subject has a medium (moderate) or low risk HLA genotype (as defined above), there is a likelihood of onset of T1D, where the total concentration of the amino acids, amino acid derivatives or amino acid metabolites; alanine, arginine, aspartate, citrulline, glycine, glutamate, glutamine, leucine, isoleucine, methionine, ornithine, phenylalanine, proline, tyrosine and valine is less than 1000 µmol/L, less than 900 µmol/L, less than 800 µmol/L or less than 700 µmol/L.

Preferably, the amino acid concentration in a subject having a medium or low risk HLA genotype is indicative of the likelihood of onset of T1D, where the above total amino acid concentration is approximately 300-1000 µmol/L, 400-900 µmol/L, 500-800 µmol/L or 600-700 µmol/L.

Most preferably, the total amino acid concentration for a subject with the medium or low risk HLA genotype is approximately 650 µmol/L.

The subject's HLA genotype and thus his/her genetic risk of developing T1D can be determined using any appropriate and available means. For instance, the subject's HLA genotype may already be known, e.g. through familial screening.

Where the HLA genotype must be determined de novo, any suitable means of genetic screening can be used. For example, a sample taken from the subject may be analyzed e.g. by PCR, serologic techniques or by DNA microarray technology. Advantageously, the technique used is PCR, for example, as described in Galgani A. Petrone A, Spoletini M, Hodge A, Del Buono M L, Locatelli M, Buzzetti R and the Diabfin Study Group. HLA class II typing in newborns reveals a low frequency of the DRB1*04 allele and a high frequency of DRB1*11 allele in three regions of continental Italy (2004), *Human Immunology* 65(4): 366-372. A sample of the subject's DNA may be obtained from the blood and any suitable body tissue or fluid, although preferably the same sample is also used for the measurement of amino acid concentrations.

The inventors have further found that the concentration of carnitine (i.e. free carnitine) and/or acylcarnitine can similarly be used in combination with a subjects HLA genotype risk category to predict the likelihood of onset of T1D.

Carnitine (L-carnitine) is a pseudo-amino acid (i.e. a dipeptide) that can be synthesized from protein-bound lysine and methionine residues. However, a human's daily requirement is generally met by food intake. Carnitine is known to help regulate fat metabolism and lower cholesterol and triglyceride levels. It is important in preventing fat build-up in the heart, and it helps to prevent the build-up of ketones (fat waste-products) in the blood. Carnitine is typically interconverted with acylcarnitine (mainly acetyl-L-carnitine), which is involved in the transportation of fatty acids across mitochondrial membranes and is thought to improve cerebral blood flow. Both molecules can be detected in e.g. a human blood sample.

Thus, in a further embodiment of the invention, the methods preferably further comprise the steps of:

(a') measuring the concentration of at least one of, free carnitine, acylcarnitine and total carnitine in a sample taken from said subject; and (d') combining the information obtained in step (a') with the information in step (c); and (e') predicting the likelihood of onset of T1D based upon the combination of step (d').

The concentration of at least one of, free carnitine, acylcarnitine and total carnitine can be used in the absence of information on the concentration of one or more amino acids to predict the likelihood of onset of T1D in a subject based on his/her HLA genotype. However, preferably, the method involves the measurement of amino acids (derivatives and metabolites) and of (total) carnitine, such that the prediction of the likelihood of onset of T1D [step (e')] is based upon the combination of step (d) and the combination of step (d').

More preferably, in step (a') the concentrations of free carnitine, acylcarnitine and total carnitine are measured.

As in the case of amino acid (derivative and metabolite) concentrations, the concentrations of carnitine (free carnitine) and/or acylcarnitine can be measured using any appropriate means. Such means are known to the person of skill in the art, and may be selected according to the above-discussed desirable features. Thus, preferably the concentration of carnitine is measured using mass spectrophotometry and more preferably using tandem mass spectrophotometry.

As in the case of amino acid concentrations, the likelihood of onset of T1D is a function of the subject's HLA genotype and the relative concentration of his/her carnitine, acylcarnitine and total carnitine. Thus, the method provides a further advantage over T1D predictions based solely on a subject's genotype.

Thus, where the subject has the high risk HLA genotype (as defined above), a likelihood of onset of T1D can be predicted when the subject's total carnitine concentration (which includes the sum of free carnitine and acylcarnitine concentrations) is less than approximately 50 μmol/L, 45 μmol/L, 42 μmol/L, 40 μmol/L or 38 μmol/L.

Preferably, the total carnitine concentration in a subject having a high risk HLA genotype is indicative of a likelihood of onset of T1D, where the above total amino acid concentration is in the range 20-50 μmol/L, 25-45 μmol/L, 28-42 μmol/L, 30-40 μmol/L or 32-38 μmol/L.

Most preferably, the total carnitine concentration for a subject with the high risk HLA genotype is approximately 35 μmol/L.

Where the subject has the medium or low risk HLA genotype (as defined above), a likelihood of onset of T1D can be predicted when the subject's total carnitine concentration is less than approximately 40 μmol/L, 35 μmol/L, 32 μmol/L, 30 μmol/L or 28 μmol/L.

Preferably, where the subject has the medium or low risk HLA genotype, the carnitine concentration is indicative of the likely future onset of T1D where the total carnitine concentration is in the range 10-40 μmol/L, 15-35 μmol/L, 18-32 μmol/L, 20-30 μmol/L or 22-28 μmol/L.

Most preferably, the total carnitine concentration for a subject with one of the medium or low risk HLA genotypes is approximately 26 μmol/L.

Advantageously, a portion or aliquot of the same sample that is used for the measurement of amino acid (derivative and metabolite) concentrations is used for the measurement of free carnitine, acylcarnitine and total carnitine. In this way, multiple samples do not necessarily have to be taken from the same subject. This is particularly beneficial where the subject is a neonate, for whom the taking of multiple samples may be a traumatic experience.

Furthermore, the sample used for measuring amino acid concentrations in step (a), or of carnitine concentrations in step (a') is the same sample that is used for determining the subject's HLA genotype. Thus, preferably a portion or aliquot of the sample used in step (a) is used for genetic screening in step (b).

Preferably, the sample taken from the subject is a body fluid sample, and more preferably the sample is a blood sample. In this regard, the concentrations of amino acids, carnitine and acylcarnitine described herein are reported as μmol per litre of blood. For other body fluids (e.g. urine and saliva) the normal and reduced concentrations of amino acids, carnitine and acylcarnitine may have to be adjusted.

Preferably the sample (e.g. blood) has been taken from the subject within 3 days (i.e. 72 hours) of the subject's birth. Thus, the subject is a neonate. As used herein, the term "neonate" refers to a person whom is less than 72 hours old.

A further advantage of the invention is that the measurements of amino acids (derivatives and metabolites) and (total) carnitine concentration can be performed reliably and accurately on a neonate, without the potential inaccuracies/misleading results that can be associated with neonatal levels of, for example, autoantibodies. This offers the potential to more reliably predict the likelihood on onset of T1D compared to prior art methods.

In addition, the speed and simplicity of the methods described herein mean that it is possible to complete the methods of the invention in the period while the subject remains a neonate. This offers the benefit that where a likelihood of onset of T1D is predicted, possible intervention therapies can be begun soon after birth (e.g. while the subject is still a neonate), which may maximize the chance of attaining an effective treatment that prevents onset of T1D later in life.

Hence, in accordance with a second aspect of the invention, there is provided a method for identifying a neonatal subject for enrolment onto a potential prophylactic treatment program for the prevention of T1D, which comprises performing the steps of any method of the invention so as to identify a neonate having a likelihood of onset of T1D and enrolling said neonate into a prophylactic treatment program.

Once a subject has been identified who has a likelihood of developing T1D, it is advantageous to begin preventative (i.e. prophylactic) therapies as soon as possible. This is particularly true in cases where the subject is a neonate.

In this regard, during the first few days of life a normal process of thymic selection eliminates virtually all potentially dangerous cytotoxic T-cells that may otherwise attack self-antigens. This process occurs as an important and necessary part of the transition from a baby that is physically connected to its mother (via the placenta), to a neonate that must become self-sufficient. Accordingly, T-cells that are autoreactive to insulin or pancreatic beta cells are typically eliminated in the thymus of normal individuals.

Without being bound by theory, it is thought that circulating amino acids and carnitine may influence the selection, development or destruction of T1D-relevant cytotoxic T-cells. It is hypothesized that low levels of amino acids and carnitine may interfere with the thymic selection process and therefore, dangerous lymphocytes escape the thymic selection, enter the subject's circulating blood and go to populate the peripheral lymphoid tissue, such as lymph nodes. The presence of such autoreactive T-cells represents a risk that that individual will develop T1D (as discussed above). Even then, it is possible that other environmental factors (e.g. viruses, dietary factors etc.) can additionally trigger the progression to the diseased state.

By initiating a T1D prophylactic treatment as early as possible in the subject's life, and particularly during the first 3 days of life, the prospects of eliminating the risk of developing T1D later in life will be increased.

Thus, in accordance with a third aspect of the invention, there is provided a method for the prophylactic treatment for T1D, which comprises the steps of:

(a) performing the steps of any of the diagnostic methods of the invention;

(b) identifying one or more subject having a likelihood of onset of T1D; and (c) prescribing to said one or more subject a prophylactic treatment for preventing or delaying the onset of T1D.

Optionally, the prophylactic treatment in step (c) comprises insulin replacement therapy.

In addition or in the alternative, the prophylactic treatment in step (c) may comprise immunomodulation therapy. Preferably, the immunomodulation therapy comprises anti-CD3 treatment and photopheresis.

In particular, it would be beneficial to influence the natural process of thymic selection in a neonate, such that a greater proportion (or all) of the auto-reactive T-cells involved in the development of T1D are destroyed before disease progression is enabled. In this way, progression to the T1D disease state may be delayed or even prevented.

In this regard, again without being bound by theory, it is thought that by administering appropriate amount of amino acids, amino acid derivatives, amino acid metabolites, and/or carnitine, to neonates having relatively low circulating levels of one or more of these molecules (i.e. low levels in view of the subject's HLA genotype risk category), then the process of thymic selection may be returned to a stringency that is sufficient to eliminate T1D-relevant auto-reactive T-cells.

Thus, in a particularly preferred embodiment of the third aspect of the invention, the prophylactic treatment in step (c) comprises a dietary supplement. More preferably, the dietary supplement comprises an amino acid, amino acid derivative or amino acid metabolite supplement. In addition or in the alternative, the dietary supplement comprises a carnitine or acylcarnitine supplement.

Accordingly, in a fourth aspect of the invention there is provided a method of treating a neonate identified as having a predisposition to T1D, comprising: administering a prophylactic composition that comprises one or more amino acid, amino acid derivative or amino acid metabolite in an amount sufficient to increase blood amino acid, amino acid derivative or amino acid metabolite levels to within the normal range.

Preferably, in the methods of the fourth aspect of the invention, the amino acid, amino acid derivative or amino acid metabolite is selected from the group consisting of: alanine, arginine, aspartate, citrulline, glycine, glutamate, glutamine, leucine, isoleucine, methionine, ornithine, phenylalanine, proline, tyrosine and valine.

More preferably, the prophylactic composition comprises all of alanine, arginine, aspartate, citrulline, glycine, glutamate, glutamine, leucine, isoleucine, methionine, ornithine, phenylalanine, proline, tyrosine and valine, and is administered in amounts sufficient to return/restore total blood amino acid, amino acid derivative or amino acid metabolite levels to within the normal range.

The prophylactic composition may comprise free carnitine and/or acylcarnitine instead of the above-listed 15 amino acids. However, in a preferred embodiment, the prophylactic composition further comprises (i.e. in addition to amino acids, derivatives and metabolites) free carnitine and/or acylcarnitine and said administering comprises administering free carnitine and/or acylcarnitine in amounts sufficient to return/restore free carnitine, acylcarnitine or total carnitine levels to within the normal range.

As the person of skill in the art will appreciate, the prophylactic compositions of the invention may be administered by any suitable means. In one embodiment, the prophylactic composition is administered orally.

Advantageously, the means of administration is suitable for neonates. In a preferred embodiment, therefore, the composition is administered parenterally, most preferably intravenously. Typically, said administering is in the form of a bolus injection, and still more preferably the composition is formulated as a slow release composition.

The time period over which the prophylactic treatment is administered may vary greatly depending on the type of treatment selected, or on the likely timescale of development of T1D. For example, it may be necessary to administer the treatment for the life of the subject, or until suitable follow-up tests demonstrate that the subject no longer has a likelihood of developing T1D. Alternatively, where a particular risk time-period can be identified, it may be sufficient to cease treatment at the end of that period. For instance, In the case of a predisposition to early-onset T1D (i.e. T1D that develops within the first 4 years of a person's life), in may be sufficient to cease treatment at the end of this 4 year period.

The skilled person in the art can determine such periods by carrying out tests for T1D indicators at relevant intervals. For example, the skilled person could repeat the diagnostic methods of the invention at repeated intervals during the individual's life, or simply measure amino acid levels at repeated intervals.

In this regard, the above timeframes of treatment may advantageously be followed for treatments such as immunomodulation therapy and/or insulin replacement therapy and/or photopheresis.

In the case of a neonate who has been identified as having a likelihood of developing T1D, however, the prophylactic treatment is preferably administered for at least the period during which the subject is classified a neonate (i.e. up to 3 days old). The period of time during which the prophylactic treatment/composition is administered may therefore vary according to when the method of the invention is carried out to predict the likelihood of onset of T1D.

Thus, where the subject is a neonate the prophylactic treatment/composition is preferably administered for at least 24 hours, at least 48 hours or at least 72 hours. Advantageously, the prophylactic treatment/composition is administered for less than 4 years, less than 3 years, less than 2 years or less than 1 year. Preferably, the prophylactic treatment/composition is administered until the subject is at least 3 days old (i.e. during the neonatal period of life).

Advantageously, during the treatment period (e.g. during the neonatal period), the prophylactic treatment is continuously effective.

The preferred form of prophylactic composition for use with neonatal subjects is a dietary supplement, and more preferably, a composition comprising one or more amino acid, amino acid derivative or amino acid metabolite and/or said free carnitine and/or acylcarnitine.

Hence, in a preferred embodiment, there is provided a method according to the fourth aspect of the invention, wherein the prophylactic composition is administered in an amount sufficient to restore to within the normal range the blood level of said one or more amino acid, amino acid derivative or amino acid metabolite and/or said free carnitine and/or acylcarnitine and maintain said normal range for the duration of the neonatal period of the subject.

Since, each individual/subject may develop at a slightly different rate, it is convenient to sometimes continue the prophylactic treatment slightly beyond the defined "neonatal period". Therefore, preferably, the above duration is at least 48 hours, more preferably at least 60 hours, and still more preferably at least 72 hours.

All references cited herein are incorporated by reference in their entirety. Unless otherwise defined, all technical and scientific terms used herein have the same meaning as commonly understood by one of ordinary skill in the art to which this invention belongs.

EXAMPLE (i) Methods

A prospective study was conducted to determine the relevance of concentration of circulating amino acids, amino acid derivatives, amino acid metabolites, free carnitine and acylcarnitine to the future development of type 1 diabetes (T1D).

Diabetic patients were identified from within the Unit of Diabetology at the Bambino Gesú Paediatric Hospital in Rome. Controls were selected from 1650 children, who were HLA typed at birth for genetic susceptibility to develop T1D (Buzzetti R. et al. 2004, *Diabetes Metab Res Rev.* 20(2): 137-43).

As a criteria of inclusion, children had be born in Lazio between January 2000 and December 2002 and T1D had to be developed by the age of 4 years. These criteria were adopted in order to: 1) have the possibility of retrieving dry blood spot samples; 2) reduce the time elapsing between birth and conducting the assays; and 3) identify controls matched for age, sex and genetic HLA risk categories (i.e. high, moderate/medium and low), defined as previously described in Buzzetti R. et al. 2004, supra.

Overall, 11 diabetic children fulfilled the selection criteria and 44 matched controls were identified. These 11 diabetic children represent nearly all of the children who have developed T1D in the first 4 years of life from a sample size of 150,000 children born in the Lazio region over the relevant time period. Information regarding the subjects used in the study is provided in Table 1.

Informed consent was obtained from parents of all children.

Information regarding birth weight, gestational age at birth and feeding in the first week of life was recorded.

Blood dry spots were retrieved from the two centers in charge of neonatal screenings (e.g. congenital hypothyroidism and phenylketonuria) in the same region. All spots were collected within the first days after birth (i.e. during the neonatal period) and stored at room temperature until the analysis. Once samples had been identified, they were coded and no information regarding T1D status was available before the results of the study had been obtained.

For each blood spot, concentrations of 15 amino acids (in 13 categories), along with the concentrations of total carnitine (TC), free carnitine (FC) and acylcarnitine (AC) were measured and recorded (see Table 2). Internal AC and amino acid standards were provided by Cambridge Isotopes Laboratories, Andover, Mass., USA.

Carnitine and amino acids were analyzed on filter paper (W903) blood spots as butyl esters. The butylated samples were tested with a tandem mass spectrometer (Sciex API 365, PE Sciex Instrument, Concord, ON, Canada). This mass spectrophotometer is routinely used for neonatal mass screening. Quality control of the methods for measuring amino acids, carnitine and acylcarnitine was performed by Dr Piero Rinaldo, (Mayo Clinic, Ronchester, Minn., USA).

TC, FC, AC and AC/FC ratio were analyzed. Amino acids were also studied as the algebraic sum of essential, non-essential and total amino acid concentrations. The Mann-Whitney U-Test was used for comparison of continuous variables. Frequencies of qualitative variables were evaluated using Fisher's exact test. A two-tailed P value of less than 0.05 was considered to be significant. All analyses were performed using SPSS 11.5.1 for Windows Package (LEAD Technologies, Inc).

(ii) Results

Referring to Table 1, among the 11 diabetic children, 4 were found to possess the high risk HLA genotype for developing T1D; 6 were found to have the medium/moderate risk HLA genotypes; and 1 had a low risk HLA genotype.

The median age at the onset of T1D was 2.7 years, and onset age ranged from 1.1 to 3.8 years.

No differences were seen in reference to gestational age at birth, birth weight and type of feeding in the first week of life (P=0.438, P=0.408 and P=0.522, respectively). Thus, in this sample it did not appear that feeding on formula milk or breast milk was relevant.

The time elapsing from the collection of blood spots to the performance of the assays was comparable in the two groups (P=0.191), so it is considered that any slight differences were insignificant.

Figure 3:
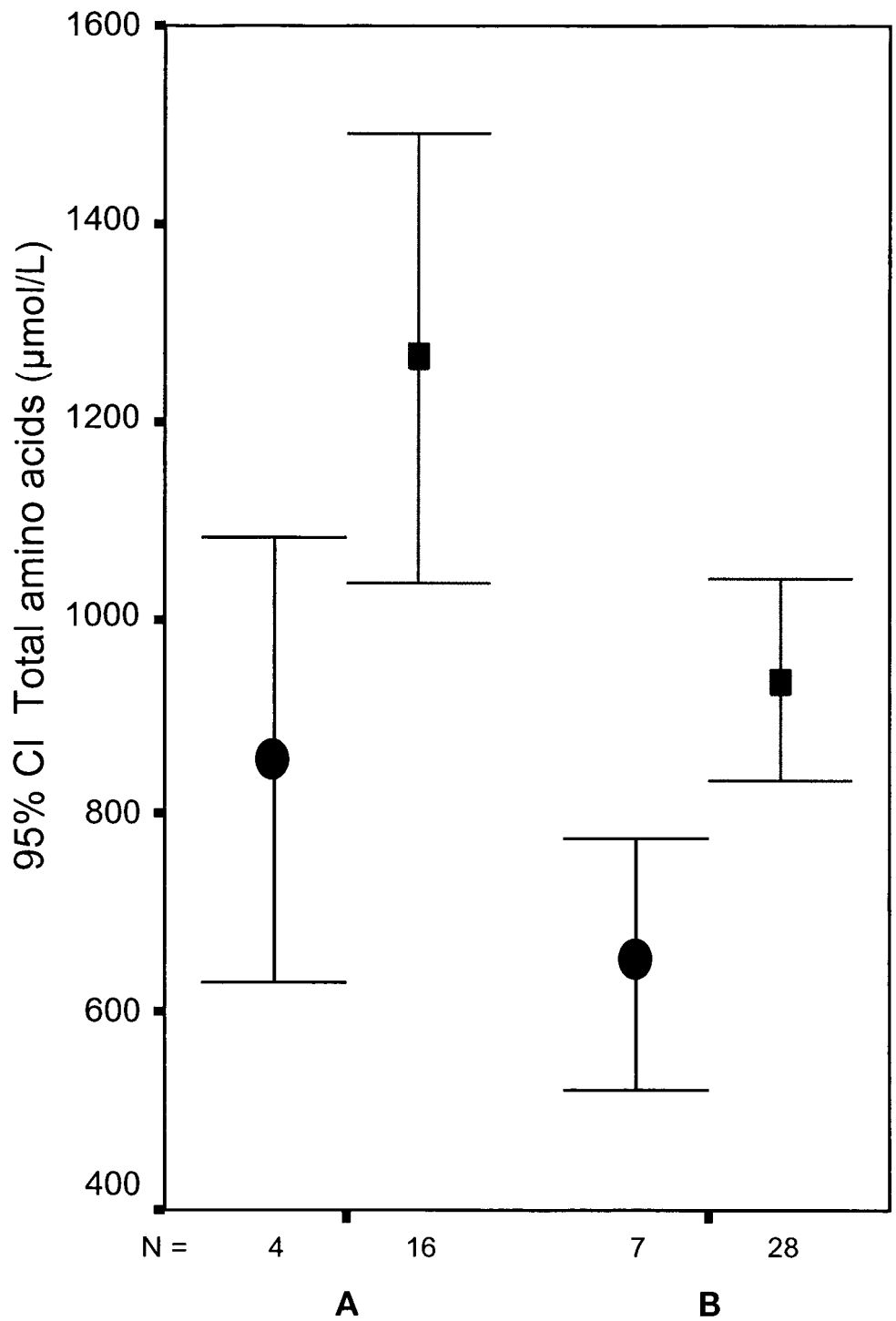
FIG. 3 is a graph showing the relationship between the total concentration of amino acids (vertical axis) in blood samples taken from T1D patients (black-filled ovals and associated bars) and non-diabetic negative controls (grey-filled rectangles and associated bars), in comparison to their HLA genotype risk category (horizontal axis): high HLA genetic risk category patients (A); and medium/moderate and low HLA genetic risk categories, grouped together (B); plotted in the 95% confidence interval. The number of subjects in each group is shown along the horizontal axis (N).

Turning to Table 2 and FIGS. 1 and 3, it can be seen that the diabetic patients displayed lower levels of all of the measured amino acids than did the non-diabetic controls. Moreover, the concentrations of the amino acids Ala, Gly, Glu/Gln, Leu/Ile, Orn, Phe and Pro were seen to be significantly lower in diabetic subjects than in the non-diabetic control subjects. Overall, total amino acid concentrations were significantly lower in diabetic patients than in controls, as were the levels of essential amino acids and non-essential amino acids. Although the concentration of the essential amino acids shown in Table 2 does not include that of arginine (which is essential in neonates), if arginine is included in the "essential" amino acid subgroup, rather than in the "non-essential" subgroup, the above observation regarding the relative levels of amino acids remains true.

FIG. 1 shows the total amino acid concentrations measured in blood samples of either T1D patients (grey-filled boxes and associated bars) or non-diabetic controls (open boxes and associated bars), depending on their HLA genotype risk category (high risk, A; and moderate/medium or low risk, B). The boxes indicate the $25^{th}$ to the $75^{th}$ percentile. In addition to the lower relative concentration of amino acids found in the samples of T1D patients, the range of total amino acid concentrations measured appears to be narrower in the T1D patients.

FIG. 3 shows the 95% confidence interval (95% CI) of the total amino acid concentrations measured in blood samples of either T1D patients (black-filled ovals and associated bars) or non-diabetic controls (grey-filled rectangles and associated bars), displayed according to the subject's HLA genotype risk category, as before (i.e. high risk, A; and moderate/medium or low risk, B). Again, it can be seen that the amino acid concentrations are significantly lower in the T1D patients than in the non-diabetic controls.

Figure 2:
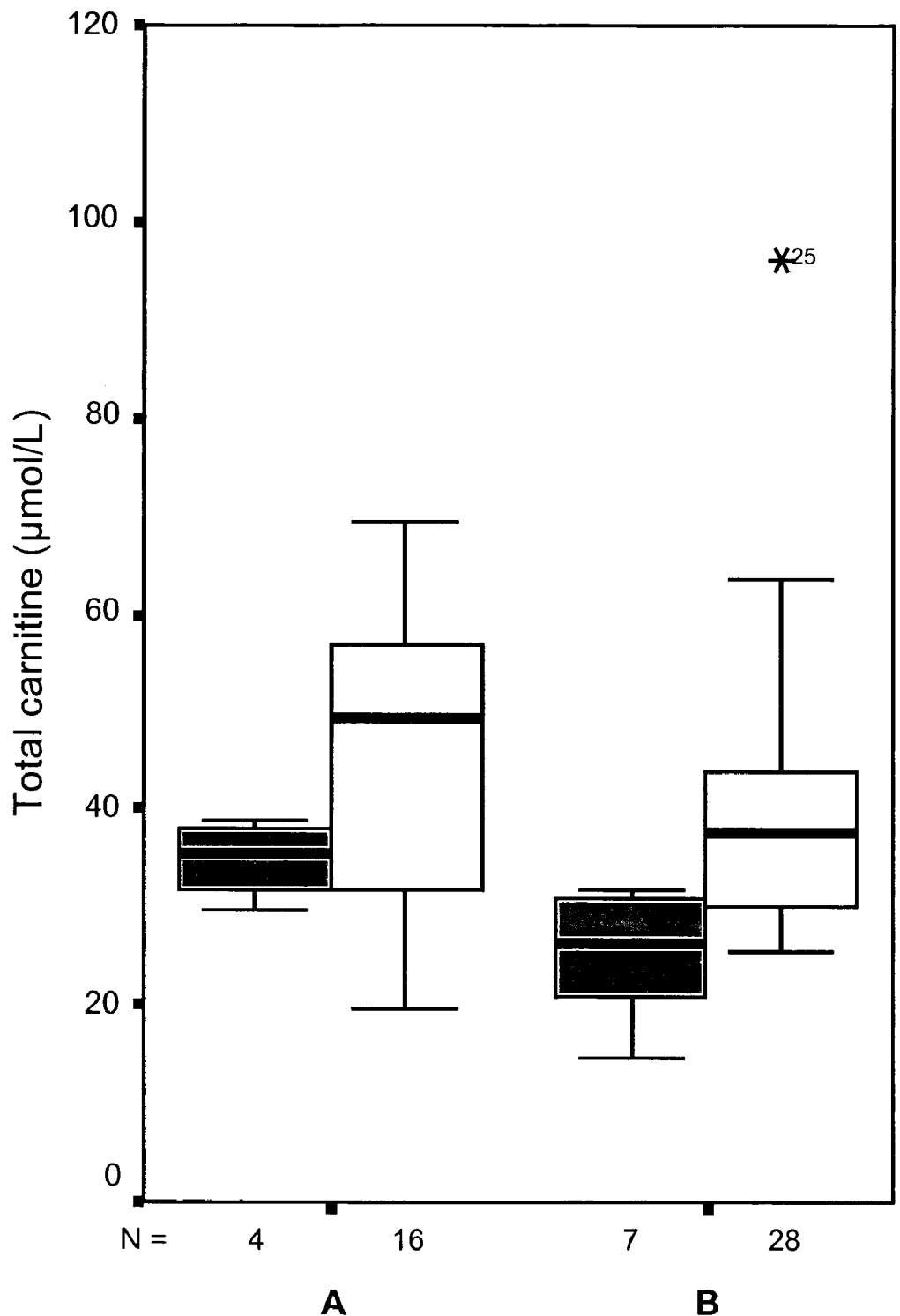
FIG. 2 is a graph showing the relationship between the total concentration of carnitine (which includes acylcarnitine; vertical axis) in blood samples taken from T1D patients (grey-filled boxes and associated bars) and non-diabetic negative controls (open boxes and associated bars), in comparison to their HLA genotype risk category (horizontal axis): high HLA genetic risk category patients (A); and medium/moderate and low HLA genetic risk categories, grouped together (B). The boxes indicate the $75^{th}$ percentile (top of box) and the $25^{th}$ percentile (bottom of box). The number of subjects in each group is shown along the horizontal axis (N).
Figure 4:
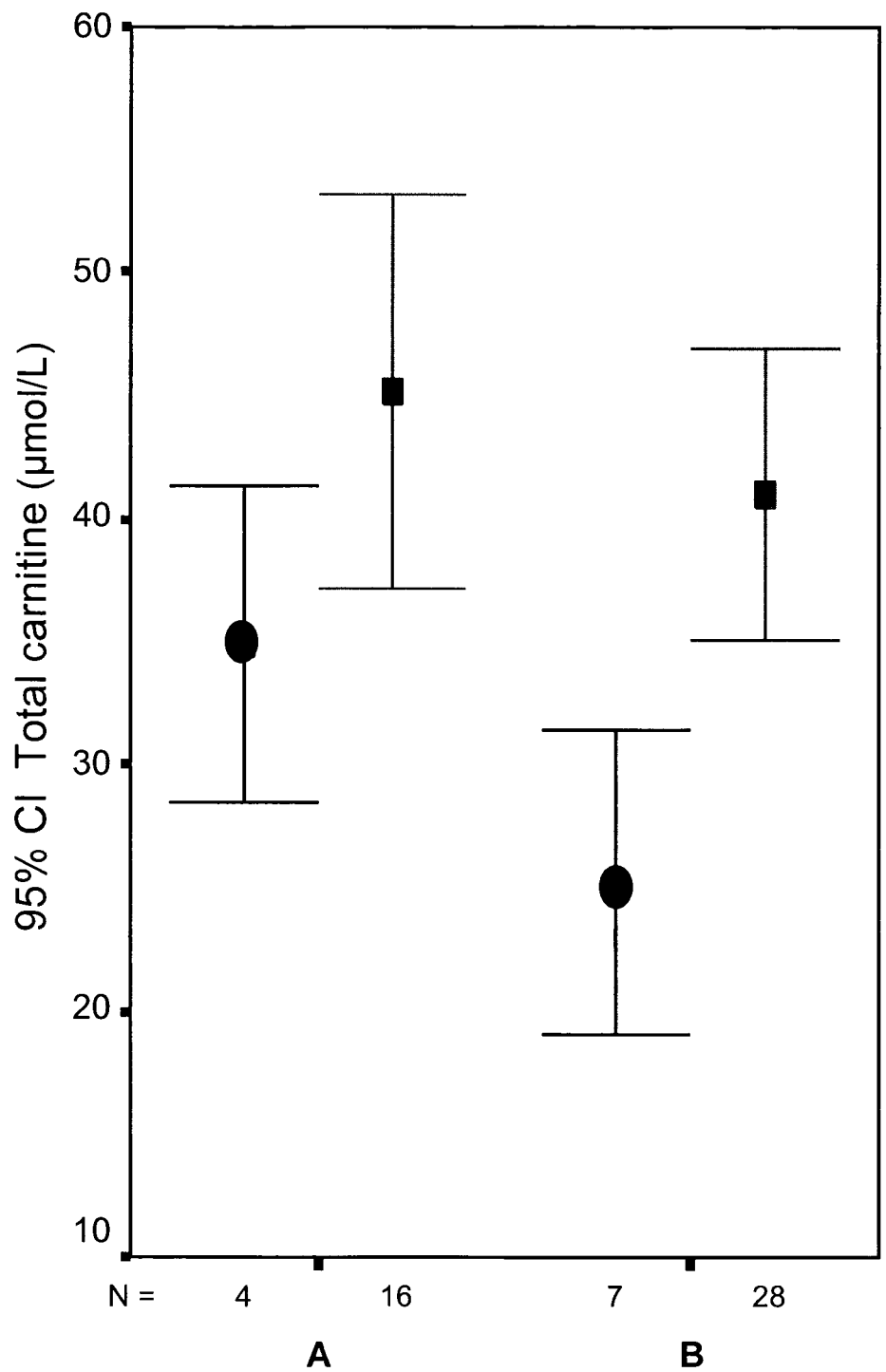
FIG. 4 is a graph showing the relationship between the total concentration of carnitine (which includes acylcarnitine; vertical axis) in blood samples taken from T1D patients (black-filled ovals and associated bars) and non-diabetic negative controls (grey-filled rectangles and associated bars), in comparison to their HLA genotype risk category (horizontal axis): high HLA genetic risk category patients (A); and medium/moderate and low HLA genetic risk categories, grouped together (B); plotted in the 95% confidence interval. The number of subjects in each group is shown along the horizontal axis (N).

Also from Table 2 and FIGS. 2 and 4, it can be seen that circulating TC, FC and AC concentrations were significantly lower in diabetic patients compared to the non-diabetic controls. However, essentially no differences were detected in the AC/FC ratio.

FIG. 2 shows the total carnitine concentrations (including acylcarnitine) measured in blood samples of either T1D patients (grey-filled boxes and associated bars) or non-diabetic controls subjects (open boxes and associated bars), depending on their HLA genotype risk category indicated as before, with high risk subjects (A), and moderate/medium or low risk subjects (B). Again, the boxes are included to indicate the $25^{th}$ to the $75^{th}$ percentile. The data shows that in addition to the lower relative amount of carnitine (and acylcarnitine) found in the samples of T1D patients, the range of total carnitine concentrations measured appears to be narrower in the T1D patients.

FIG. 4 shows the 95% confidence interval (95% CI) of the total carnitine concentrations measured in blood samples of either T1D patients (black-filled ovals and associated bars) or non-diabetic control subjects (grey-filled rectangles and associated bars), displayed according to the subject's HLA genotype risk category, categories as already discussed. As before, it can be seen that the carnitine concentrations are significantly lower in the T1D patients than in the non-diabetic controls.

The data used in FIGS. 1 and 2 is displayed in Table 3 and the data used in FIGS. 3 and 4 is displayed in Table 4.

(iii) Conclusions

This is the first demonstration that neonates who go on to develop T1D early in life (i.e. in the first 4 years) display reduced concentrations of amino acids and of carnitine during the neonatal period.

Since this investigation was carried out retrospectively on dried blood spots stored at room temperature, as a control, 80 dried blood spots taken from children of the same region, and which have undergone similar storage conditions in the same centers for two and four years, respectively, have been tested using the same tandem mass spectrometer used for the Example.

Values of amino acids and of TC, FC and AC, were measured and found to be very similar in the two sample sets (inventors' unpublished results). In the Example described, since the time elapsing between blood collection and the conduction of the assays was similar between diabetics and controls, and was carried out in the time range of 2-4 years, the differences in amino acid and carnitine concentrations noted between diabetics and non-diabetic controls can be considered not to be due to the latency between blood collection and sample testing.

For the reasons already discussed with regard to Table 1, it is also possible to exclude the differences in the type of feeding, because the proportion of children whom were breast-fed or whom were fed formula milk was comparable between the two groups.

It is therefore concluded that children who later developed T1D early in life have reduced levels of circulating amino acids and carnitine at birth or soon after birth (i.e. during the neonatal period). Thus, low levels of amino acids and of carnitine may be viewed as additional markers for predicting the future onset of T1D in children, irrespective of their perceived genetic susceptibility.

The determination of these compounds is easy to do and can be routinely applied in population screenings. Hence, new perspectives for the testing of all newborn children, to predict the likely onset of T1D, and if necessary commence a suitable prophylactic treatment regime are apparent.

TABLE 1

Characteristics of diabetic children and matched controls

|  | Diabetic Patients (N = 11) | Control children (N = 44) | Significance P |
|---|---|---|---|
| M:F | 7:4 | 28:16 | — |
| HLA risk category | | | |
| high | 4 | 16 | — |
| moderate | 6 | 24 | |
| low | 1 | 4 | |
| Gestational age at birth (weeks) | 39 (37-41) | 39 (30-41) | 0.438 |
| Birth weight (Kg) | 3.5 (3.0-4.1) | 3.4 (1.6-4.8) | 0.408 |
| Feeding during the 1$^{st}$ week | | | |
| only breast milk | 6 | 26 | 0.522 |
| formula or mixed | 5 | 18 | |
| Age at onset of T1D (yrs) | 2.7 (1.1-3.8) | — | — |
| Age at metabolic evaluation (yrs) | 3.9 (2.5-5.0) | 3.2 (1.6-4.9) | 0.191 |

Values are expressed as number of cases or as median (range).

TABLE 2

Carnitine and amino acid concentrations (μmol/L) in blood dry spots collected within the first three days of life

|  | Diabetic Patients (N = 11) | Control children (N = 44) | Significance P |
|---|---|---|---|
| Total carnitine | 29.9 (14.8-38.9) | 39.5 (19.7-96.1) | 0.004 |
| Free carnitine | 19.0 (6.8-25.6) | 24.7 (11.7-68.9) | 0.009 |
| Acylcarnitine | 10.7 (7.8-16.3) | 16.5 (8.0-27.2) | 0.009 |
| Acyl/free ratio | 0.7 (0.4-1.2) | 0.6 (0.3-1.2) | 0.556 |
| Alanine (Ala) | 82.5 (50.7-174.4) | 140.8 (50.1-526.7) | 0.037 |
| Arginine (Arg) | 15.1 (10-34.6) | 17.4 (7.3-49.0) | 0.599 |
| Aspartate (Asp) | 35.9 (15.8-70.4) | 42.9 (18.0-152.9) | 0.461 |
| Citrulline (Cit) | 4.6 (2.9-13.3) | 6.8 (2.4-22.1) | 0.064 |
| Glycine (Gly) | 80.9 (49.8-131.2) | 122.1 (66.0-354.7) | 0.002 |
| Glutammate/Glutammine (Glu/Gln) | 223.8 (114.4-332.1) | 314.0 (211.2-578.1) | 0.002 |
| *Leucine/Isoleucine (Leu/Xle) | 60.9 (42.2-84.6) | 86.9 (51.5-191.2) | <0.001 |
| *Methionine (Met) | 3.6 (1.9-8.2) | 4.4 (1.3-10.9) | 0.326 |
| Ornitine (Orn) | 6.7 (4.0-16.8) | 11.0 (3.4-34.8) | 0.001 |
| *Phenylalanine (Phe) | 15.2 (3.9-29.8) | 24.9 (12.4-54.8) | 0.001 |
| Proline (Pro) | 45.3 (24.4-73.7) | 73.9 (34.2-128.5) | 0.002 |
| Thyrosine (Thy) | 26.4 (14.1-65.2) | 32.3 (13.7-80.3) | 0.323 |
| *Valine (Val) | 59.8 (29.8-150) | 67.8 (10-250) | 0.192 |
| Essential aminoacids | 134 (91-242) | 177 (120-426) | 0.003 |
| Non essential aminoacids | 549 (424-852) | 781 (465-1805) | 0.003 |
| Total aminoacids | 677 (515-1016) | 954 (618-2230) | 0.003 |

Values are expressed as median (range)
*Essential amino acids (excluding arginine)

TABLE 3

Total amino acid and carnitine concentrations measured in samples taken from subjects with either the high risk HLA genotype or with the moderate or low risk HLA genotypes (as plotted in FIGS. 1 and 2 respectively)

|  | high risk diabetics (Nr = 4) | high risk controls (Nr = 16) | moderate or low risk diabetics (Nr = 7) | moderate or low risk controls (Nr = 28) |
| --- | --- | --- | --- | --- |
| Total amino acids (µmol/L) | | | | |
| maximum | 1016.4 | 2231 | 909.6 | 1628.3 |
| 75th percentile | 996.4 | 1543 | 677.2 | 1191.7 |
| median | 836.8 | 1229.6 | 673.3 | 849 |
| 25th percentile | 735.8 | 960.5 | 520.5 | 715.9 |
| minimum | 735.2 | 618.5 | 515.6 | 632.2 |
| Total carnitine (µmol/L) | | | | |
| maximum | 38.9 | 69.6 | 31.8 | 96.1 |
| 75th percentile | 38.4 | 57.1 | 31.78 | 44.8 |
| median | 35.4 | 49.2 | 26.4 | 37.8 |
| 25th percentile | 30.7 | 31.8 | 18.9 | 30.2 |
| minimum | 29.7 | 19.7 | 14.8 | 25.3 |

TABLE 4

Total amino acid and carnitine concentrations measured in samples taken from subjects with either the high risk HLA genotype or with the moderate or low risk HLA genotypes (as plotted in FIGS. 3 and 4 respectively)

|  | high risk diabetics (Nr = 4) | high risk controls (Nr = 16) | moderate or low risk diabetics (Nr = 7) | moderate or low risk controls (Nr = 28) |
| --- | --- | --- | --- | --- |
| Total amino acids (µmol/L) | | | | |
| 95% CI upper limit | 1082.9 | 1493.4 | 774.5 | 1039.7 |
| 95% CI lower limit | 629.8 | 1035.6 | 523.2 | 833.2 |
| 95% CI midpoint | 856.3 | 1264.5 | 648.8 | 936.5 |
| Total carnitine (µmol/L) | | | | |
| 95% CI upper limit | 41.3 | 53.2 | 31.3 | 46.9 |
| 95% CI lower limit | 28.4 | 37.1 | 19.1 | 35.1 |
| 95% CI midpoint | 34.9 | 45.1 | 25.2 | 41 |

The invention claimed is:

1. A composition comprising;
   carnitine and acylcarnitine; and
   one or more amino acids;
   wherein said composition is adapted for use in a method of treating a healthy neonate identified as having a predisposition to Type 1 Diabetes (T1D).

2. A composition according to claim 1, wherein the one or more amino acids are selected from the group consisting of alanine, arginine, asparagines, aspartate, cysteine, glutamate, glutamine, glycine and histidine.

3. A dietary supplement for use in the prophylactic treatment of Type 1 Diabetes, said dietary supplement comprising the composition of claim 1.

* * * * *